United States Patent
D'Angelo

[19]

[11] Patent Number: 5,910,122
[45] Date of Patent: Jun. 8, 1999

[54] SALIVA COLLECTOR WITH AN ASPIRATING PIPETTE

[75] Inventor: Joseph P. D'Angelo, Miami, Fla.

[73] Assignee: Americare Health Scan Inc., Miami, Fla.

[21] Appl. No.: 08/869,098

[22] Filed: Jun. 4, 1997

Related U.S. Application Data

[60] Provisional application No. 60/017,835, Jun. 4, 1996.

[51] Int. Cl.$^6$ ........................................................ A61B 5/00
[52] U.S. Cl. ............................ 600/573; 600/580; 604/317
[58] Field of Search ................................... 600/573, 580, 600/349, 365, 581, 582; 604/317

[56] References Cited

U.S. PATENT DOCUMENTS

| | | | |
|---|---|---|---|
| 3,640,268 | 2/1972 | Davis | 128/2 B |
| 4,596,157 | 6/1986 | Laauwe | 600/580 |
| 4,774,962 | 10/1988 | Hebel et al. | 600/573 |
| 4,817,632 | 4/1989 | Schramm | 600/582 |
| 5,078,968 | 1/1992 | Nason | 600/580 |
| 5,334,502 | 8/1994 | Sangha | 600/573 |
| 5,376,337 | 12/1994 | Seymour | 600/573 |
| 5,380,492 | 1/1995 | Seymour | 600/573 |
| 5,460,782 | 10/1995 | Coleman et al. | 600/573 |

*Primary Examiner*—Max Hindenburg
*Assistant Examiner*—Charles Marmor, III
*Attorney, Agent, or Firm*—Herbert L. Lerner; Laurence A. Greenberg

[57] ABSTRACT

Saliva samples are collected for body fluid constituent analysis by placing a sponge member into a patient's oral cavity. The sponge member is formed similarly to a pacifier nipple. Saliva is absorbed. The saliva is then expelled from the sponge member into a pipette. A filter may be placed between the sponge member and the pipette, through which the saliva is cleaned and molecular weight-selectively prepared by letting only substances through with a molecular weight below a cut-off weight. The integral unit is dismembered after the saliva has been transferred into the collection pipette, and the latter is tightly closed off for further handling.

13 Claims, 4 Drawing Sheets

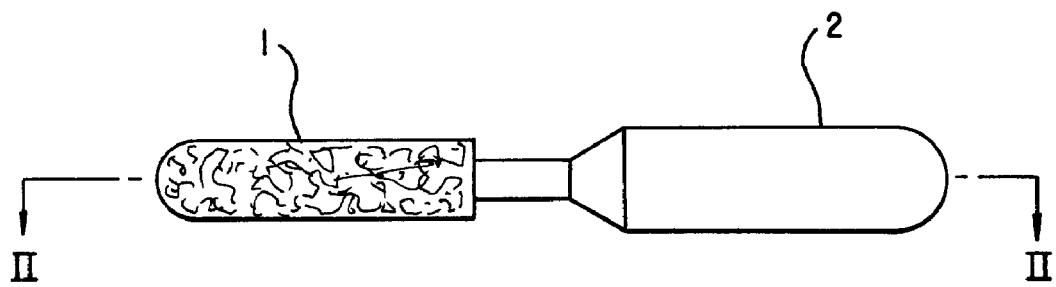
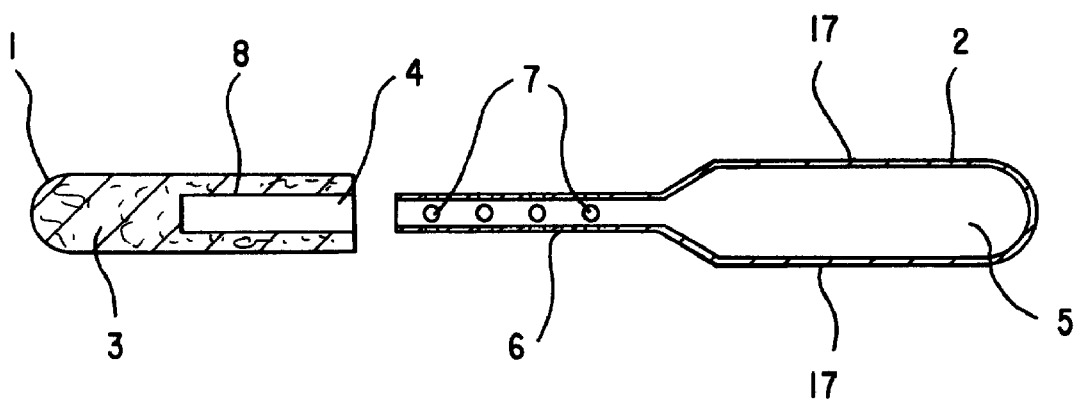

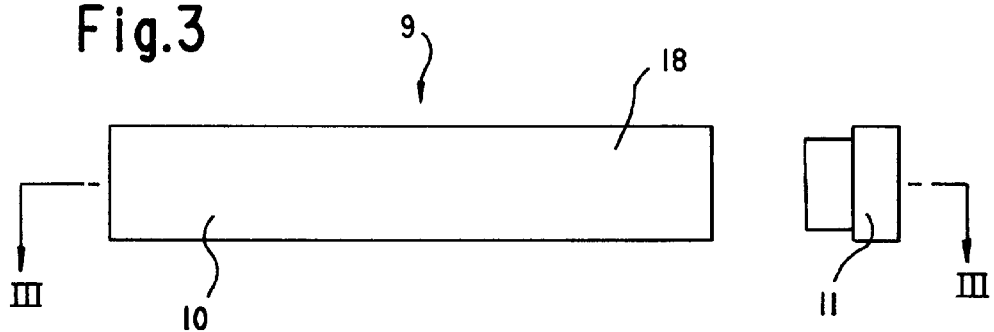
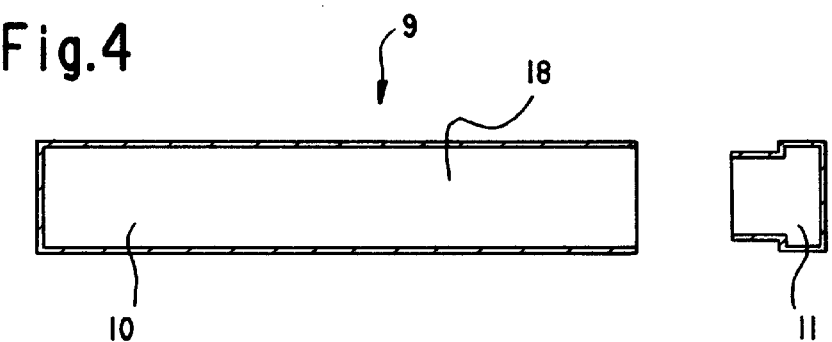
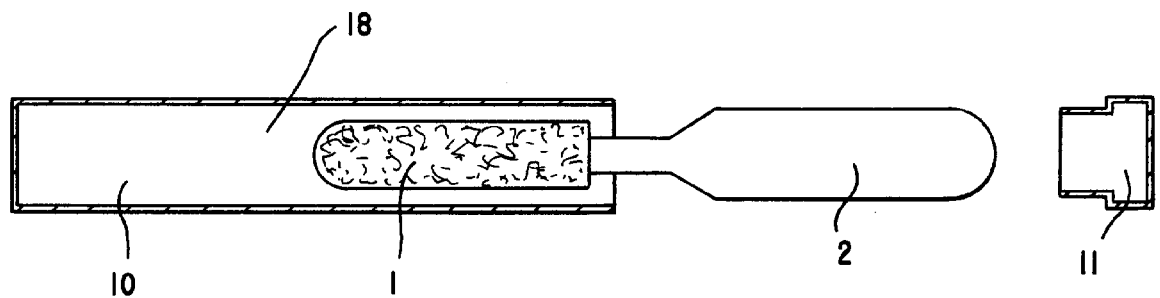
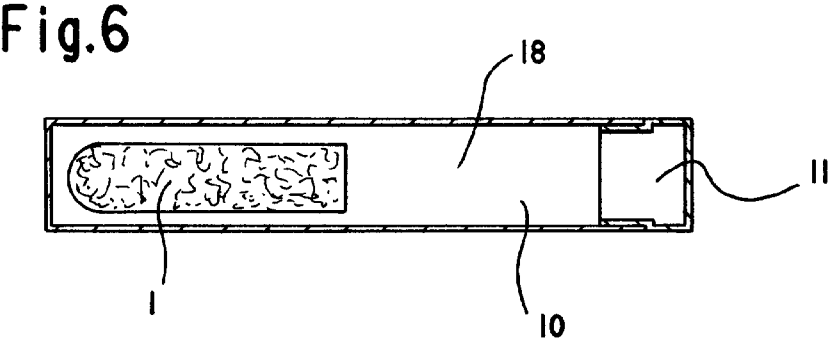

SALIVA COLLECTOR WITH AN ASPIRATING PIPETTE

CROSS-REFERENCE TO RELATED APPLICATION

This application claims the benefit, under 35 U.S.C. §119(e), of my prior provisional application Ser. No. 60/017,835 filed Jun. 4, 1996.

BACKGROUND OF THE INVENTION

1. Field of the Invention

The invention relates to a system for collecting samples of saliva for body fluid constituent analysis.

2. Description of the Related Art

Saliva testing has recently come to the forefront as a preferred option in body fluid constituent analysis. The collection procedure is non-invasive, and saliva has been found to be a very reliable carrier of analyte indicators. For instance, PKU tests on infants are now regularly done, drug abuse is tested in many circumstances, HIV testing may be relatively reliably performed with saliva, and levels of therapeutic drugs may be ascertained through saliva testing.

A recent advance in saliva collection and test preparation is disclosed in U.S. Pat. No. 5,103,836 to Goldstein et al. An absorbent pad which is impregnated with a salt of a hypertonic solution is inserted into the mouth and saliva is brushed off from the cavity walls. After having absorbed a sufficient amount of saliva, the pad is removed and stored in a vial for later testing. The test kit is suited for immunoglobulin collection and testing for immunological information in the body fluid. That prior art test provides enough saliva for only a single test, i.e. the saliva is not collected for general, multiple testing.

Another saliva collector is disclosed in U.S. Pat. No. 5,268,148 to Seymour. A portion of filter paper is exposed so that, when enough saliva is collected, the paper will provide an indication that the collected amount is adequate.

The method and apparatus described in U.S. Pat. No. 4,774,962 to Hebel et al. allows extracting saliva from the human body in that a sponge member is chewed for a certain amount of time and after saliva has been absorbed in the sponge member, it is centrifuged therefrom. The method may be acceptable for adult saliva collection. Such a free sponge, however, is essentially unsuitable for infant testing due to the danger of ingestion and it is also not acceptable in view of the proposed utilization thereof in HIV and hepatitis testing.

The prior art devices have in common that the collection of saliva sample is rather cumbersome, it exposes the medical worker to dangerous substances, and/or the amount of saliva thus collected is inadequate to perform various tests. Also, none of the prior art devices provide a convenient method and kit for collecting a large amount of saliva for body fluid constituent analysis. Finally, saliva collection from very small infants, for instance for PKU testing, is quite difficult and virtually always accompanied by forcing the infant's mouth open during the procedure.

SUMMARY OF THE INVENTION

It is accordingly an object of the invention to provide a saliva collector with an aspirating pipette, which overcomes the hereinafore-mentioned disadvantages of the heretofore-known devices of this general type and which provides a self-contained collection and test kit as well as a reliable and convenient method of collecting saliva samples for general, multiple testing. Finally, it is an object to provide a fully integrated, sterile package, which allows collecting and handling without any danger of exposure to the medical worker.

With the foregoing and other objects in view there is provided, in accordance with the invention, a method of collecting saliva samples for body fluid analysis. The method comprises the following steps:

providing an absorptive saliva collector with a collection pipette;

placing the saliva collector with the collection pipette into a patient's oral cavity and absorbing saliva into the absorptive saliva collector;

squeezing the collection pipette for drawing the saliva out of the absorptive saliva collector and into the collection pipette; and removing the absorptive saliva collector with the collection pipette from the patient's oral cavity.

The method is continued with the step of separating the collection pipette from the absorptive saliva collector.

The method is further continued with the providing step providing the absorptive saliva collector selected from the group consisting of polyurethane, polyethylene, polypropylene, and cellulose.

With the foregoing and other objects in view there is provided, in accordance with the invention, an assembly for collecting saliva for body fluid analysis, comprising an absorptive saliva collector to be placed into a patient's oral cavity for absorbing saliva therein; and a collection pipette contiguous with the absorptive saliva collector, the collection pipette having elastically resilient walls adapted to collapse towards one another upon being squeezed and, upon expanding, driving the saliva from the absorptive saliva collector into the collection pipette.

In accordance with an additional feature of the invention, the absorptive saliva collector is formed of a material selected from the group consisting of polyurethane, polyethylene, polypropylene, and cellulose.

In accordance with another feature of the invention, the absorptive saliva collector is formed from water-catalyzed polyurethane.

In accordance with an added feature of the invention, the absorptive saliva collector has a sponge member which is formed as a pacifier nipple.

In accordance with yet another additional feature of the invention, the absorptive saliva collector has a recess formed therein and includes a filter member residing in the recess for filtering particulate matter.

In accordance with yet another feature of the invention, there is a collection container defining a cavity adapted to receive the absorptive saliva collector and the collection pipette.

In accordance with yet another added feature of the invention, the absorptive saliva collector is impregnated with a flavor substance for stimulating the patient's saliva production.

In accordance with an additional feature of the invention, there is a pipette cover for fluid-tightly sealing the collection pipette.

In accordance with another feature of the invention, the collection pipette has a plurality of openings formed therein for allowing fluidic communications between the absorptive saliva collector and the collection pipette.

In accordance with yet another feature of the invention, there is a chemical test reagent disposed in the collection pipette.

In accordance with a concomitant feature of the invention, the collection container has a top and includes a cap for fluid-tightly sealing the top of the collection container, a saliva collector storage tube for storing the absorptive saliva collector and a pipette storage tube for storing the collection pipette.

Although the invention is illustrated and described herein as embodied in a saliva collector with an aspirating pipette, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

BRIEF DESCRIPTION OF THE DRAWINGS

FIG. 1 is an elevational view of a saliva collector engaging an aspirating pipette according to the invention;

FIG. 2 is an exploded, sectional view of the saliva collector and the aspirating pipette taken along the line II—II shown in FIG. 1;

FIG. 3 is an exploded, elevational view of a storage container for the saliva collector and the aspirating pipette;

FIG. 4 is an exploded, sectional view of the storage container taken along the line III—III shown in FIG. 3;

FIG. 5 is an exploded, partially broken away view of the storage case containing the saliva collector and the aspirating pipette partially contained in the storage container;

FIG. 6 is a partially broken away view of the storage container holding the saliva collector;

DESCRIPTION OF THE PREFERRED EMBODIMENTS

Figure 7:
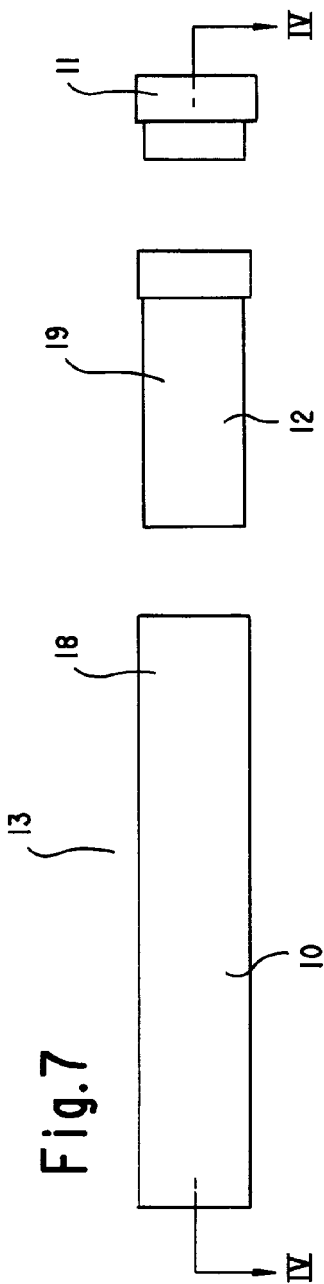
FIG. 7 is an exploded, elevational view of a three piece storage case.
Figure 8:
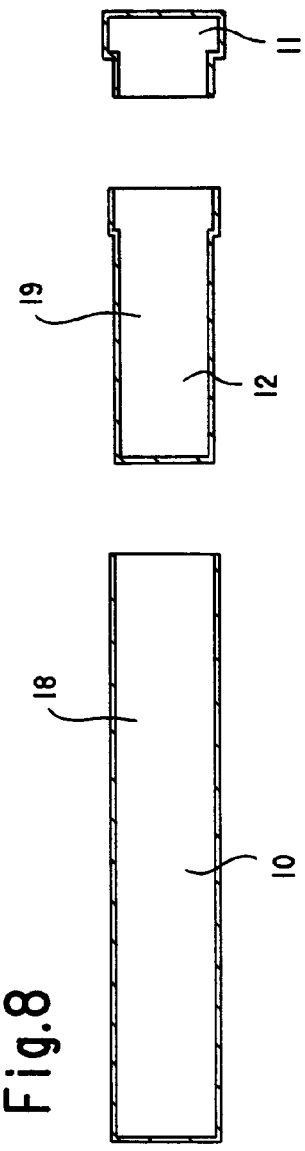
FIG. 8 is an exploded, sectional view of the three piece storage container taken along the line IV—IV shown in FIG. 7.
Figure 9:
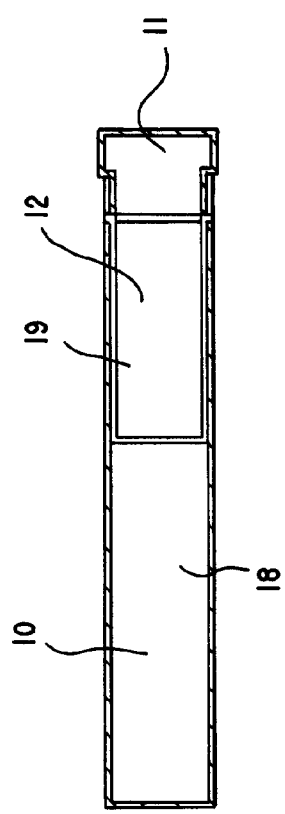
FIG. 9 is a sectional view of the three piece storage container shown in FIG. 7.

Referring now to the figures of the drawing in detail and first, particularly, to FIG. 1 thereof, there is seen an absorptive saliva collector 1 and a collection or aspirating pipette 2.

FIG. 2 shows a sectional view of the saliva collector 1 and the aspirating pipette 2. The saliva collector 1 has a sponge member 3 formed with a recess 4 on one end of the sponge 3 member. The sponge member 3 is formed similarly to a pacifier nipple. The aspirating pipette 2 has a saliva storage container 5 and a saliva receiving shaft 6. The saliva receiving shaft 6 is formed with a plurality of openings 7.

The openings 7 allow the entry of saliva entrapped in the sponge member 3 into the saliva storage container 5. The aspirating pipette 2 having elastically resilient walls 17 adapted to collapse towards one another upon being squeezed and to drive the saliva from the saliva collector 1 into the aspirating pipette 2. The aspirating pipette 2 is formed of a thin, i.e. squeezable material.

The size of the openings 7 can also be set to serve as a filter for limiting the size of particles that can enter the saliva storage container 5. In the alternative, the recess 4 can receive a mesh filter 8 to limit the size of particles that are allowed to enter the saliva storage container 5. The mesh filter membrane may be adjusted to any mesh density. By way of example, a 10,000 MW (molecular weight) membrane may be used for cleaning the saliva. Other mesh sizes are also possible, depending on the specimen requirements.

The recess 4 of the sponge member 3 engages the saliva receiving shaft 6 of the aspirating pipette 2. The sponge member 3 is made from either polypropylene, polyethylene, polyurethane, cellulose, or blends thereof. More specifically, the sponge member 3 is formed of water-catalyzed polyurethane and it is preferably formed of HYPOL, available from Hampshire Chemical Corporation. That material has a very high absorption density and excellent tensile strength. Similar materials may be used. Factors to be considered, however, are that the material must be largely inert, it must not easily break so as to prevent any ingestion of solid material, and it must have good absorptive qualities. Additionally, as will become clear from the following description, it should be able to release all or most of the saliva previously collected under the pressure exerted by the aspirating pipette 2.

FIG. 3 shows a storage container 9 formed of a storage tube 10 having a cavity 18 and a cap 11 configured to store the saliva collector 1 and the aspirating pipette 2. FIG. 4 shows a sectional view of the storage tube 10 and the cap 11. FIG. 5 shows a partially broken away view of the saliva collector 1 and the aspirating pipette 2 entering the storage tube 10. FIG. 6 shows a view of the storage tube 10 and the cap 11 enclosing the saliva collector 1.

Figure 10:
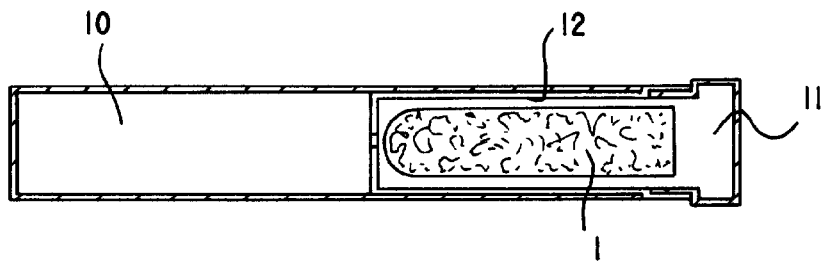
FIG. 10 is a partially broken away view of the assembled three piece storage container holding the saliva collector.

FIGS. 7–10 show a three-piece storage container 13 formed of the storage tube 10, the cap 11 and a saliva collector storage tube 12 having a cavity 19 for receiving the saliva collector 1. FIG. 10 shows the saliva collector 1 contained in the saliva collector storage tube 12 which in turn is sealed in the storage tube 10.

Figure 11:
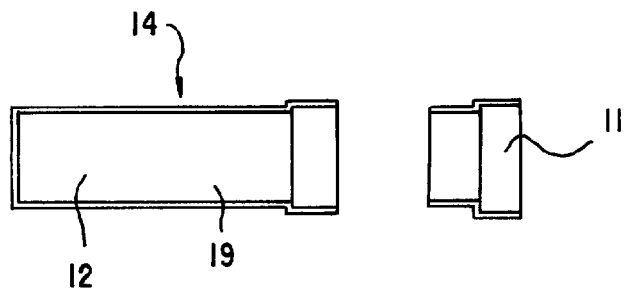
FIG. 11 is an exploded, elevational view of a saliva collector storage container.
Figure 12A:
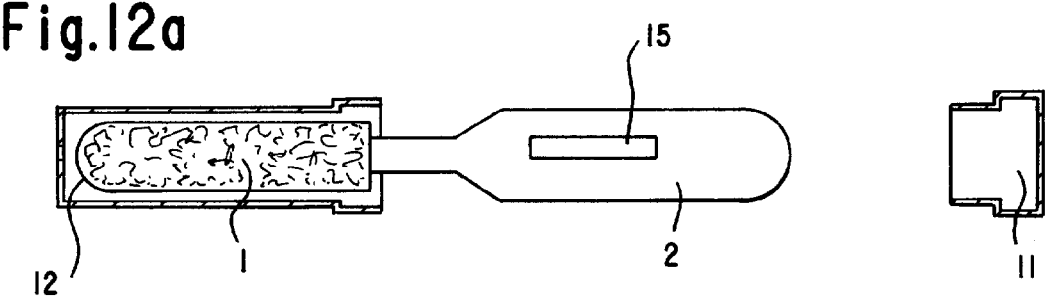
FIGS. 12a and 12b are exploded, partially broken away views of the saliva storage container holding the saliva collector.
Figure 12B:
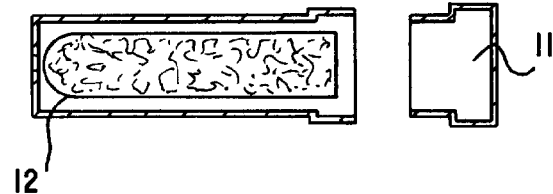

FIGS. 11 and 12 show a saliva collector storage container 14 formed of the saliva collector storage tube 12 and the cap 11. FIG. 12b shows the saliva collector 1 sealed in the saliva collector storage tube 12. As shown in FIG. 12a, a frosted area 15 may be provided on the aspirating pipette 2, so as to allow proper labeling.

In operation, the saliva collector 1 engaging the aspirating pipette 2 is inserted in the subjects mouth. After the sponge member 3 has resided in the subjects mouth for at least 20 seconds (up to 5 minutes), the aspirating pipette 2 can be squeezed resulting in the suction of the saliva into the aspirating pipette 2. The aspirating pipette 2 can be continuously squeezed until the aspirating pipette 2 contains the desired amount of saliva. For that purpose it is clear that the aspirating pipette 2 is formed of transparent or translucent material, or that a viewing window is provided.

Because the saliva is collected in the aspirating pipette 2, the saliva has been filtered by the sponge member 3, the openings 7 and the mesh filter 8. Therefore, a particulate free saliva has been collected. A major advantage of the invention is that the saliva does not contain contaminates such as food particles which can cause erroneous test results.

To facilitate the saliva collection, the absorptive saliva collector 1 may be impregnated with a flavor substance for stimulating a patient's saliva production.

In a further embodiment, the assembly is provided for a specific test application. In that case, one end of the aspirating pipette 2 holds a certain chemical reactant. When the saliva comes into contact with the reaction chemical, an indication is triggered. That indication may, for instance, be in the form of a colorimetric reaction. For that purpose it is clear that the aspirating pipette 2 is formed of transparent or translucent material, or that a viewing window is provided. General information on saliva testing is available from "Saliva as a Diagnostic Fluid", Malamud and Tabak, Editors; Annals of the New York Academy of Sciences; Vo. 694; Sep. 20, 1993.

The embodiment is based on the premise that saliva testing by colorimetry and the like has recently seen a flurry of novel developments which are all hindered by the fact that the prior art systems for collecting the saliva are typically cumbersome and slow, and/or the amount of saliva thus harvested is often not sufficient. The recent call for full disposability of such devices is answered by this invention.

Figure 13:
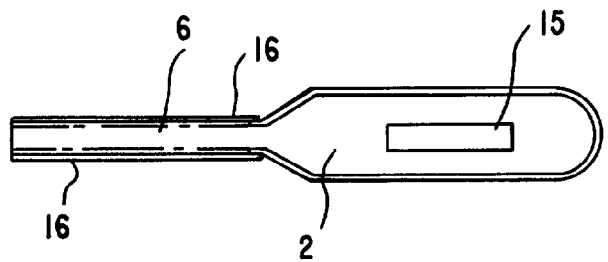
FIG. 13 is an elevational view of the aspirating pipette with a pipette cover.

FIG. 13 shows the aspirating pipette 2 with a pipette cover 16 which is placed over the shaft 6 of the aspirating pipette 2 to prevent saliva from leaking out of the aspirating pipette 2. The pipette cover 16 has a simple friction fit to the aspirating pipette 2. It is also possible to fit the shaft 6 and the pipette cover 16 with mutually threaded meshes. In this manner, the saliva can be stored in the aspirating pipette 2.

After saliva has been transmitted to the aspirating pipette 2, the saliva collector 1 can be returned to the storage container 9, 13, 14 for a sanitary disposal of the saliva collector 2. In this same manner, the aspirating pipette 2 can also be disposed in the storage container 9, 13. The cap 11 is securely fastened to the storage tubes 10,12. A simple friction fit between the storage tubes 10,12 and the cap 11 will in most cases suffice. It is also possible, however, to provide the cap 11 and the storage tube 10 or the saliva collector storage tube 12 with mutually meshing threads. The storage tubes 10,12 are preferably formed as a polypropylene, polyethylene or styrene cylinder. The saliva collector storage tube 12 can also be frictionally fitted to the storage tube 10 or in the alternative be provided with mutually threaded mesh.

I claim:

1. An assembly for collecting saliva for body fluid analysis, comprising:

an absorptive saliva collector to be placed into a patient's oral cavity for absorbing saliva therein, said absorptive saliva collector having a recess formed therein;

a collection pipette contiguous with and fluidically connected to said absorptive saliva collector, said collection pipette having elastically resilient walls adapted to collapse towards one another upon being squeezed and, upon expanding, driving the saliva from said absorptive saliva collector into said collection pipette; and a filter member residing in said recess of said absorptive saliva collector for filtering particulate matter.

2. The assembly according to claim 1, wherein said absorptive saliva collector is formed of a material selected from the group consisting of polyurethane, polyethylene, polypropylene, and cellulose.

3. The assembly according to claim 1, wherein said absorptive saliva collector is formed from water-catalyzed polyurethane.

4. The assembly according to claim 1, wherein said absorptive saliva collector has a sponge member which is formed as a pacifier nipple.

5. The assembly according to claim 1, including a collection container defining a cavity adapted to receive said absorptive saliva collector and said collection pipette.

6. The assembly according to claim 5, wherein said collection container has a top and includes a cap for fluid-tightly sealing said top of said collection container, a saliva collector storage tube for storing said absorptive saliva collector and a pipette storage tube for storing said collection pipette.

7. The assembly according to claim 1, wherein said absorptive saliva collector is impregnated with a flavor substance for stimulating the patient's saliva production.

8. The assembly according to claim 1, including a pipette cover for fluid-tightly sealing said collection pipette.

9. The assembly according to claim 1, wherein said collection pipette has a plurality of openings formed therein for allowing fluidic communications between said absorptive saliva collector and said collection pipette.

10. The assembly according to claim 1, which further comprises a chemical test reagent disposed in said collection pipette.

11. A method of collecting saliva samples for body fluid analysis, which comprises:

providing an absorptive saliva collector with a collection pipette;

placing the saliva collector with the collection pipette into a patient's oral cavity and absorbing saliva into the absorptive saliva collector;

squeezing the collection pipette for drawing the saliva out of the absorptive saliva collector and into the collection pipette; and removing the absorptive saliva collector with the collection pipette from the patient's oral cavity.

12. The method according to claim 11, which further includes the step of separating the collection pipette from the absorptive saliva collector.

13. The method according to claim 11, wherein the step of providing comprises providing the absorptive saliva collector selected from the group consisting of polyurethane, polyethylene, polypropylene, and cellulose.

* * * * *